US012697039B2

(12) United States Patent
Zhu et al.

(10) Patent No.: US 12,697,039 B2
(45) Date of Patent: Aug. 4, 2026

(54) WEARABLE BIOIMPEDANCE MONITORING SYSTEM USING CONFORMAL NANOWIRE ELECTRODES

(71) Applicant: North Carolina State University, Raleigh, NC (US)

(72) Inventors: Yong Zhu, Raleigh, NC (US); Alper Bozkurt, Raleigh, NC (US); William D. Reynolds, Jr., Raleigh, NC (US); Shuang Wu, Raleigh, NC (US); Tanner Panithan Songkakul, Raleigh, NC (US)

(73) Assignees: NORTH CAROLINA STATE UNIVERSITY, Raleigh, NC (US); ONDA VISION TECHNOLOGIES, INC., Raleigh, NC (US)

( * ) Notice: Subject to any disclaimer, the term of this patent is extended or adjusted under 35 U.S.C. 154(b) by 594 days.

(21) Appl. No.: 17/977,596

(22) Filed: Oct. 31, 2022

(65) Prior Publication Data

US 2023/0136435 A1 May 4, 2023

Related U.S. Application Data

(60) Provisional application No. 63/273,378, filed on Oct. 29, 2021.

(51) Int. Cl.
*A61B 5/0537* (2021.01)
*A61B 5/00* (2006.01)
*A61B 5/0531* (2021.01)

(52) U.S. Cl.
CPC .......... *A61B 5/0537* (2013.01); *A61B 5/0015* (2013.01); *A61B 5/0531* (2013.01);
(Continued)

(58) Field of Classification Search
CPC ... A61B 5/0537; A61B 5/0531; A61B 5/7225; A61B 2562/164; A61B 5/053
See application file for complete search history.

(56) References Cited

U.S. PATENT DOCUMENTS 6,151,523 A * 11/2000 Rosell Ferrer ....... A61B 5/4869
600/506
6,236,212 B1 * 5/2001 Wynn ...................... G01V 3/06
324/365

(Continued)

OTHER PUBLICATIONS

Analog Realization of Fractional-Order Skin-Electrode Model for Tetrapolar Bio-Impedance Measurements. Technologies 2020, 8(4), 61. (Year: 2020).*

*Primary Examiner* — Christian Jang
(74) *Attorney, Agent, or Firm* — Thomas | Horstemeyer, LLP

(57) ABSTRACT

Various examples are related to bioimpedance measurements. In one example, a wearable monitoring system includes electrodes and processing circuitry configured for bioimpedance sensing. The electrodes can include a current source electrode, a current sink electrode, and voltage measurement electrodes aligned between the current source and sink electrodes. The processing circuitry can sense bioimpedance based upon excitation current applied through the current source and sink electrodes and measured voltage obtained through the voltage measurement electrodes across a range of excitation frequencies. The electrodes can be conformal and stretchable. In another example, a method for bioimpedance sensing includes positioning a wearable monitoring system on a surface, applying excitation current through the current source and sink electrodes over a range of excitation frequencies; measuring voltage across the voltage measurement electrodes over the excitation frequencies; and determining the bioimpedance using the applied (Continued)

excitation current and the measured voltage over the excitation frequencies.

20 Claims, 10 Drawing Sheets

(52) U.S. Cl.
CPC .......... *A61B 5/6801* (2013.01); *A61B 5/7225*
(2013.01); *A61B 2562/0215* (2017.08); *A61B*
*2562/0219* (2013.01); *A61B 2562/164*
(2013.01)

(56) References Cited

U.S. PATENT DOCUMENTS

| | | | | |
|---|---|---|---|---|
| 6,301,500 B1 * | 10/2001 | Van Herk | ............ | A61N 1/0476 |
| | | | | 607/148 |
| 6,909,781 B1 * | 6/2005 | Itri | ........................ | H04M 3/304 |
| | | | | 379/399.01 |
| 2002/0123694 A1 * | 9/2002 | Organ | .................. | A61B 5/0536 |
| | | | | 73/1.01 |
| 2003/0216663 A1 * | 11/2003 | Jersey-Willuhn | ...... | A61B 5/412 |
| | | | | 977/932 |
| 2006/0116599 A1 * | 6/2006 | Davis | ................... | A61B 5/0536 |
| | | | | 600/547 |
| 2013/0332085 A1 * | 12/2013 | Yang | ................... | G01N 27/416 |
| | | | | 702/22 |
| 2014/0275888 A1 * | 9/2014 | Wegerich | ............... | A61B 5/053 |
| | | | | 600/324 |
| 2016/0338639 A1 * | 11/2016 | Myers | ................... | A61B 5/681 |

* cited by examiner

Square Electrodes          Circular Electrodes

Wearable Bioimpedance Multivariate Time Series Output

| | |
|---|---|
| • | 5 kHz |
| ✶ | 10 kHz |
| ◆ | 15 kHz |
| × | 25 kHz |
| ✦ | 50 kHz |
| ✗ | 95 kHz |
| ✻ | 195 kHz |

Resistance (Ω)

Time (n)

1 cm

| Sample | 1 | 2 | 3 |
|--------|---|---|---|
| Slope | 2.286 ± 0.031 | 14.78 ± 1.849 | 24.10 ± 1.512 |
| R² | 0.9992 | 0.9410 | 0.9844 |

| Sample | 1 | 2 | 3 |
|--------|---|---|---|
| Slope | 18.68 ± 2.826 | 54.83 ± 3.952 | 105.6 ± 6.506 |
| R² | 0.9161 | 0.9796 | 0.9850 |

| Sample | 1 | 2 | 3 |
|---|---|---|---|
| Slope | -6.937 ± 0.5402 | -28.42 ± 4.032 | -34.84 ± 3.513 |
| R² | 0.9992 | 0.9255 | 0.9609 |

| Sample | 1 | 2 | 3 |
|---|---|---|---|
| Slope | -5.972 ± 1.324 | -2.611 ± 1.435 | -9.679 ± 0.9629 |
| R² | 0.8357 | 0.4528 | 0.9619 |

WEARABLE BIOIMPEDANCE MONITORING SYSTEM USING CONFORMAL NANOWIRE ELECTRODES

CROSS REFERENCE TO RELATED APPLICATIONS

This application claims priority to, and the benefit of, U.S. provisional application entitled "WEARABLE BIO-IMEPEDANCE MONITORING SYSTEM USING CON-FORMAL AgNW ELECTRODES" having Ser. No. 63/273, 378, filed Oct. 29, 2021, which is hereby incorporated by reference in its entirety.

STATEMENT REGARDING FEDERALLY SPONSORED RESEARCH OR DEVELOPMENT

This invention was made with government support under grant number IIP1949908 awarded by the National Science Foundation. The government has certain rights in the invention.

BACKGROUND

Monitoring hydration level is vital for maintaining physiological and cognitive performance during physical exertion and thermal stress. Water content of the body plays a key role in maintaining homeostasis and various physiological functions. More than 2% weight loss from dehydration may lead to decreased physical and cognitive performance in humans. Measuring hydration is especially crucial to the safety and performance of several professionals such as athletes, first responders or military personnel performing intense physical activities under harsh environmental conditions.

SUMMARY

Aspects of the present disclosure are related to bioimpedance measurements. In one aspect, among others, a wearable monitoring system comprises a plurality of electrodes and processing circuitry configured for bioimpedance sensing. The plurality of electrodes can comprise one or more current source electrode, one or more current sink electrode, and voltage measurement electrodes aligned between the current source and sink electrodes. The plurality of electrodes can be conformal and stretchable nanowire electrodes (e.g., silver nanowire (AgNW) electrodes). The processing circuitry can be configured for bioimpedance sensing based upon excitation current applied through the current source and sink electrodes and measured voltage obtained through the voltage measurement electrodes across a range of excitation frequencies.

In one or more aspects, the processing circuitry can comprise an impedance analog front end (AFE) coupled to the plurality of electrodes. The impedance AFE can comprise DC isolation for each of the plurality of electrodes. The impedance AFE can measure voltage across the voltage measurement electrodes and current through the current sink electrode. The measurements can be obtained at a plurality of frequencies in the range of excitation frequencies. The processing circuitry can calculate an impedance at each of the plurality of frequencies.

In various aspects, the nanowire electrodes can comprise a network of AgNWs. The AgNWs can be inlaid in a soft polymer matrix. The soft polymer matrix can comprise Poly(dimethylsiloxane) (PDMS). The current source electrode, current sink electrode, and voltage measurement electrodes can each have a defined area and a defined spacing between the other electrodes. The processing circuitry can calculate an impedance at each of a plurality of frequencies within the range of excitation frequencies. The processing circuitry can transmit data associated with the impedance to a remotely located data aggregator. The processing circuitry can comprise an accelerometer and the transmitted data comprises motion data obtained from the accelerometer.

In another aspect, a method for bioimpedance sensing comprises positioning a wearable monitoring system on a surface, the wearable monitoring system comprising a plurality of electrodes comprising one or more current source electrode, one or more current sink electrode, and voltage measurement electrodes aligned between the current source and sink electrodes; applying excitation current through the current source and sink electrodes over a range of excitation frequencies; measuring voltage across the voltage measurement electrodes over the range of excitation frequencies; and determining the bioimpedance based upon the applied excitation current and the measured voltage over the range of excitation frequencies. In one or more aspects, the measured voltage can be obtained at a plurality of frequencies in the range of excitation frequencies. An impedance can be calculated at each of the plurality of frequencies.

In various aspects, the method can comprise transmitting data associated with the bioimpedance to a remotely located data aggregator. The method can comprise monitoring motion of the wearable monitoring system. The transmitted data can comprise motion data obtained by the wearable monitoring system. The surface can be a skin surface. The plurality of electrodes can comprise conformal and stretchable silver nanowire (AgNW) electrodes. The method can comprise producing multivariate time series measurements over the range of excitation frequencies. The method can comprise producing a bioimpedance profile with continuous resistivity and phase measurements over the range of excitation frequencies. The method can comprise directly measuring impedance of extracellular and intracellular water components over a small area of the surface.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
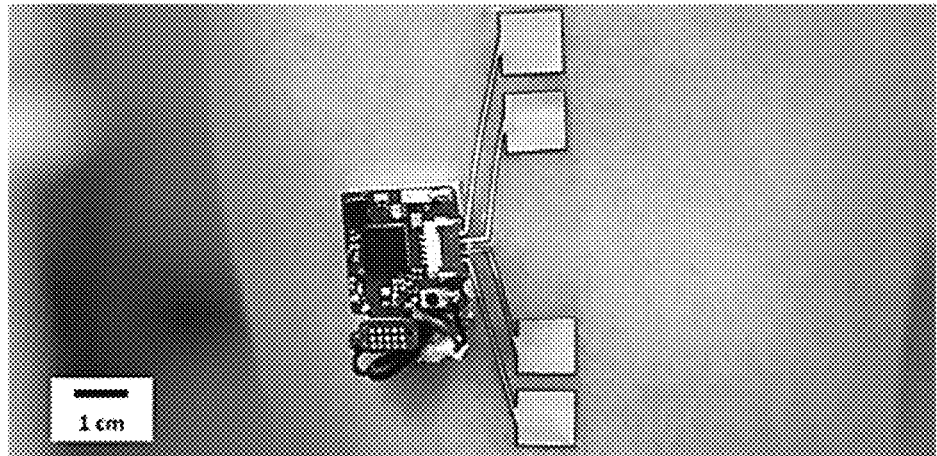
FIG. 1 is an image of an example of the wearable continuous hydration monitoring system, in accordance with various embodiments of the present disclosure.

Disclosed herein are various examples related to bioimpedance measurements. For example, a miniaturized, customized and wearable bioimpedance spectroscopy system comprising a Bluetooth-enabled system-on-a-chip and an analog front-end circuit that is integrated with conformable, flexible, and stretchable nanowire based sensors is disclosed. This system can perform bipolar or four-electrode bioimpedance spectroscopy with real-time in-depth bioimpedance measurements over a range of frequencies between 0.015 Hz and 200 kHz, transmitting the data wirelessly to a data aggregator, and configuring the front-end circuit parameters over-the-air when needed. A four-probe sensor can be used to eliminate interference from contact resistances and capacitances with traditional two-probe sensors. A 150 mAh LiPo battery can power the system for 18 hours or more.

Use of the system can provide real-time and accurate hydration sensing. In-vitro validation of the system has generated promising results. In addition to hydration monitoring, the system can provide monitoring for cancer (chemotherapy treatment), chemotherapy-induced adverse events, chemotherapy toxicity and prognosis, radiotherapy-induced adverse events, lymphedema, sickle cell disease, diabetes, nephrotic syndrome, cell health and integrity, chronic hydration, hemodialysis, peritoneal dialysis, inflammation detection, chronic obstructive pulmonary disease (COPD), insulation resistance, metabolic syndrome, noninvasive tissue characterization, nutrition analysis, congenital heart disease (CHD), chronic kidney disease (CKD), wound healing, edema, tissue ischemia, agricultural heat related illness, or other conditions. Reference will now be made in detail to the description of the embodiments as illustrated in the drawings, wherein like reference numbers indicate like parts throughout the several views.

While qualitative visual signs such as skin turgor or sunken eyes provide some indication of hydration, more quantitative methods are needed to confidently and accurately assess the hydration level. These include loss of weight, osmolality and composition of various body fluids, as well as properties of skin (e.g., bioimpedance, thermal conductance, etc.). However, most of these methods are suitable only for clinical settings.

Monitoring the real-time hydration level of an active subject can be facilitated using a miniaturized system design. The bioimpedance sensing system has the potential to be used in a wearable form factor. Advancements in the manufacturing of conformable and stretchable electrodes have facilitated the development of wearable bioimpedance monitoring systems.

Several designs have shown the feasibility of bioimpedance spectroscopy (BIS) in measuring the hydration level. However, there is still a need for further miniaturization and more efficient skin interfacing. With an aim of developing a comfortably wearable system, a miniaturized bioimpedance sensing system equipped with conformal silver nanowire (AgNW) electrodes was designed. Other metal nanowires (e.g., gold (Au), copper (Cu), nickel (Ni), etc.) and other conductive nanowires (e.g., conductive polymers) can be utilized for the nanowire electrodes. In this disclosure, the sensor design can be improved by modifying the electrode topology and structure to obtain more accurate and deeper measurements. FIG. 1 is an image of an example of the wearable continuous hydration monitoring system comprising custom wireless bioimpedance spectroscopy electronics and conformable silver nanowire electrodes. The electronic readout system can also be further miniaturized and improved. In-vitro evaluation results are presented demonstrating the successful operation of the system.

Material and Methods

Figure 2A:
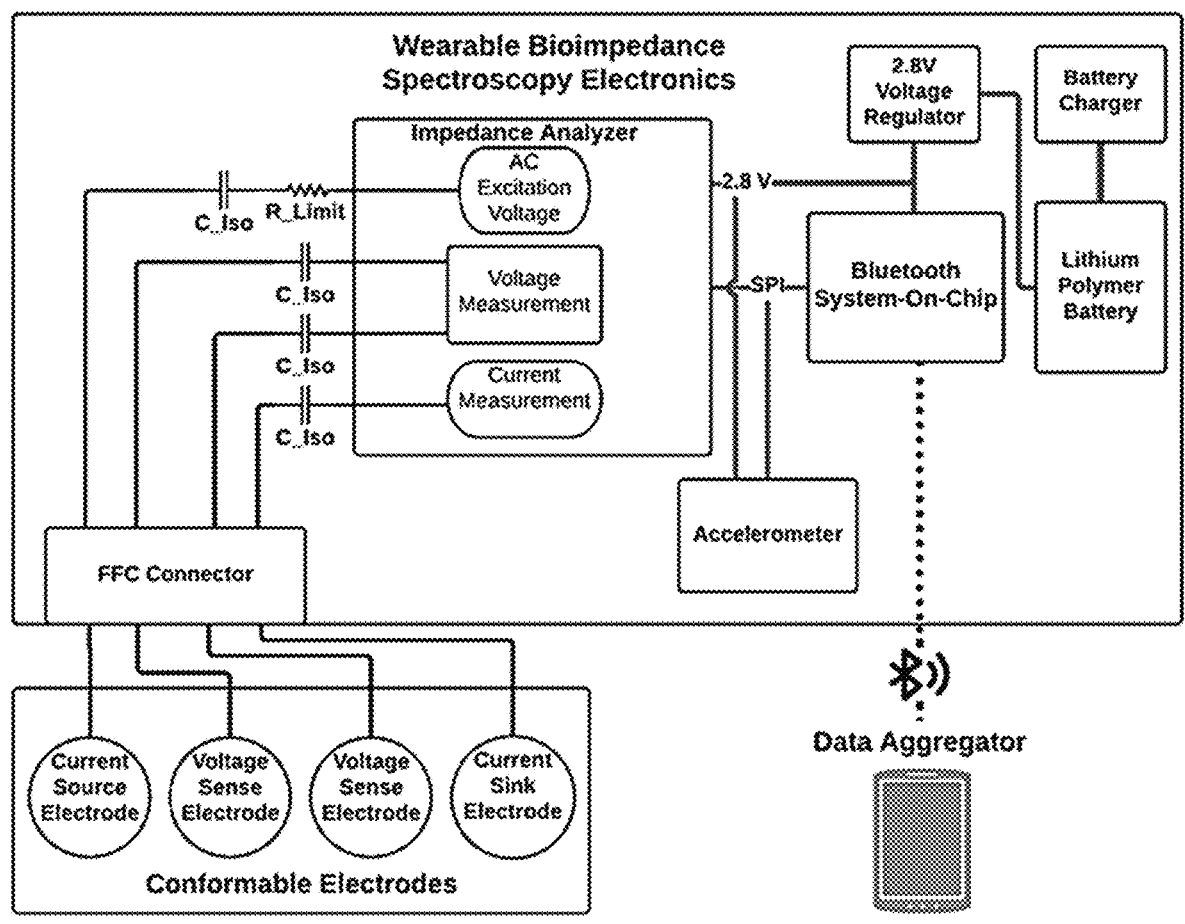
FIG. 2A is a block diagram illustrating an example of the system electronics, in accordance with various embodiments of the present disclosure.

Wearable Bioimpedance Spectroscopy System Electronics. FIG. 2A is a block diagram illustrating an example of the system electronics. The custom miniaturized electronic system for wearable bioimpedance spectroscopy can comprise a system-on-a-chip (SoC) (e.g., CC2642, Texas Instruments) equipped with Bluetooth Low Energy (BLE) interfacing an impedance analog front end (AFE) (e.g., AD5941, Analog Devices, Inc. (ADI)) configured for multi-electrode BIS. Two of the electrodes act as the current source and sink, and voltage is measured across the other two electrodes. The current tetrapolar configuration reduces the effect of the electrode, tissue, and electrode-tissue interface impedances, relative to a bipolar configuration, by separating the excitation and sensing circuits. For example, the system can be configured for safety employing a peak AC current is limited to 400 µA by, e.g., a 1 kΩ resistor, and 0.47 µF capacitors provide DC isolation to the electrodes. A Discrete Fourier Transform (DFT) can be applied on a series of data samples to find the magnitude and phase of the excitation current and measured voltage to calculate the impedance.

The AFE can be connected directly to custom conformable electrodes with, e.g., a ribbon cable connector (e.g., FH12-5S-1SH(55), Hirose Electric Co. Ltd.). During measurement, the AFE can continuously sample voltage and current signals across a range of excitation frequencies and can transmit the raw data back to the SoC. The SoC can calculate the impedance for each frequency and can wirelessly transmit the sweep data to a data aggregator via BLE, WiFi or other wireless communications. The user can also wirelessly configure the frequency sweep range and steps, output data rate (ODR), DFT size, etc. The AFE can be capable of sweeping any frequency range from 0.015 Hz to 200 kHz. An example system configuration includes a complete a frequency sweep as fast as every 51 ms for a 10-point sweep with a DFT length of 1024. The system can also contain a 3-axis accelerometer (e.g., ADXL362, ADI) for recording activity levels and motion artifacts. The system can be powered by a battery (e.g., a 3.7 V 150 mAh Lithium Polymer battery) regulated to a defined voltage (e.g., 3.3 V) by a linear voltage regulator (e.g., ADP160, ADI).

Figure 2B:
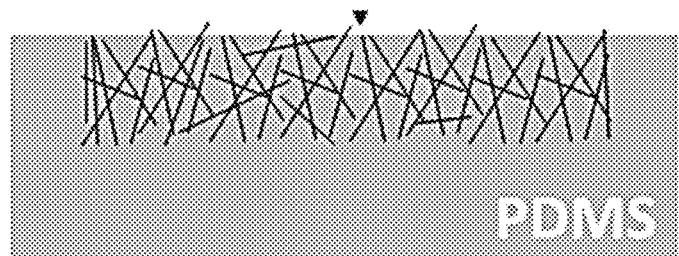
FIGS. 2B-2D illustrate examples of nanowire electrodes, in accordance with various embodiments of the present disclosure.
Figure 2C:
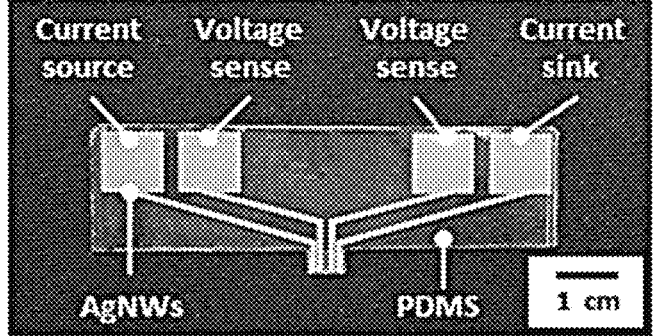
Figure 2D:
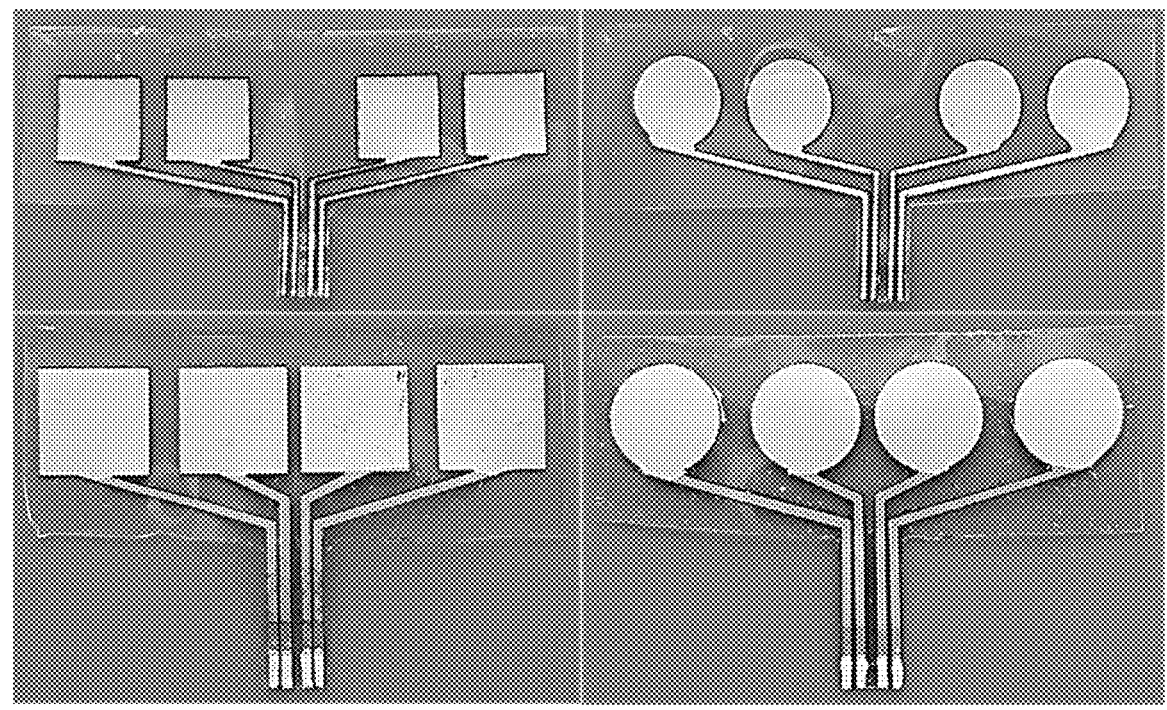

Conformable Nanowire Sensor Fabrication. A modified polyol process was used to prepare AgNW segments with an average diameter of 90 nm and length of 20-30 μm. The prepared AgNW in ethanol solution was drop-casted on plasma-treated polyimide (PI) tape on a glass slide. At the same time, the solution was heated by a hot plate at 50° C. to evaporate the solvent. After the evaporation of ethanol, the AgNWs were thermally annealed at 150° C. for 20 min. Then the sample was laser cut to the desired pattern with excess nanowires and PI removed. Poly(dimethylsiloxane) (PDMS) precursor (e.g., SYLGARD 184, Dow Inc.) with a weight ratio of 10:1 was spin-coated onto the AgNW film, degassed, and subsequently cured at 100° C. for 1 hour such that the AgNWs were half-embedded below the top surface of PDMS. FIG. 2B illustrates a cross-sectional diagram of silver nanowire electrodes embedded in PDMS substrate. The connector interface end of the AgNWs traces can be reinforced with Ag epoxy (e.g., 8330S, MG Chemicals Ltd.) for stable connection to the printed circuit board. For example, each of the excitation and voltage sensing electrodes can be configured for a 1 cm² in area, with a 6 cm separation between the current source and sink, and a 3.7 cm separation between the voltage sense electrodes. FIG. 2C is an image showing an of the conformable nanowire electrodes. FIG. 2D includes images showing other possible configurations for the conformable nanowire electrodes with square electrodes on the left and circular electrodes on the right. The overall sensor is 7.5 mm×2.5 cm and weighs 0.09 g.

Figure 3A:
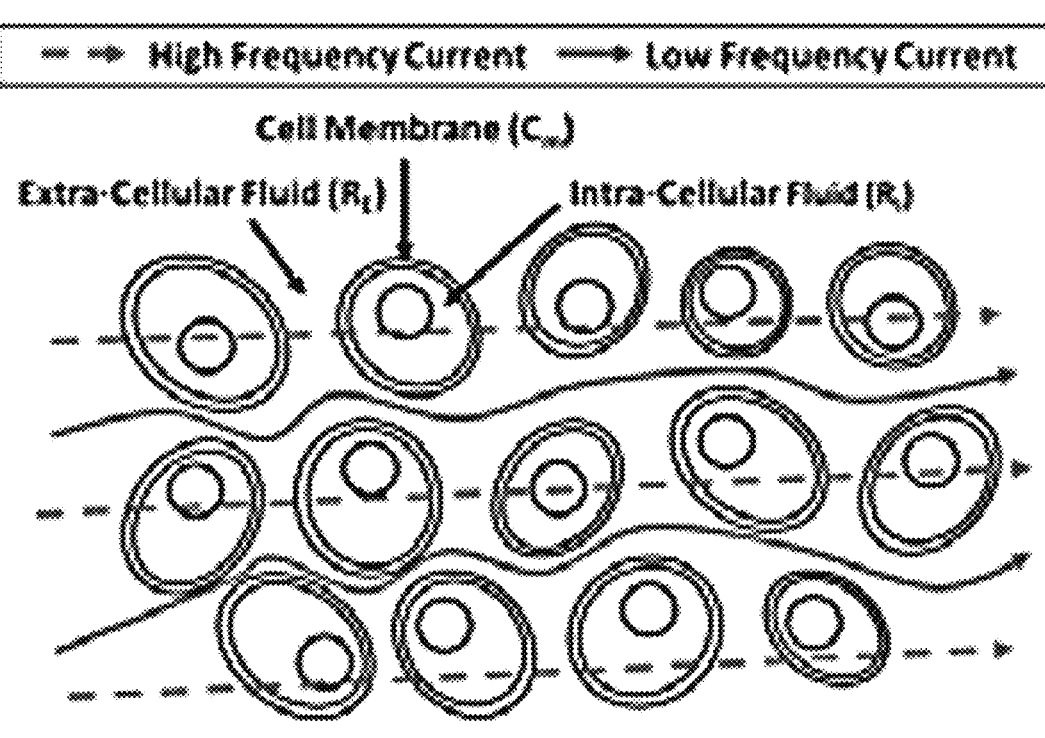
FIGS. 3A and 3B illustrate examples of current through tissue and a tissue circuit equivalent model, in accordance with various embodiments of the present disclosure.

Circuit Model Validation. During BIS, electrical current traveling through the human body can be modeled as a single-dispersion RC circuit model. A resistor $R_E$ represents the extracellular fluid around the cells, while a parallel capacitor $C_m$ in series with a resistor $R_I$ represent the cell membrane capacitance and intracellular fluid, respectively. FIG. 3A illustrates an example of the path of high and low frequency current through tissue. The impedance of the tissue circuit model can then be expressed as follows:

$$Z(f) = \frac{R_I \cdot R_E}{R_I + R_E} + \frac{R_E - \frac{R_I \cdot R_E}{R_I + R_E}}{1 + j2\pi f(R_I + R_E) \cdot C_m}$$

Figure 3B:
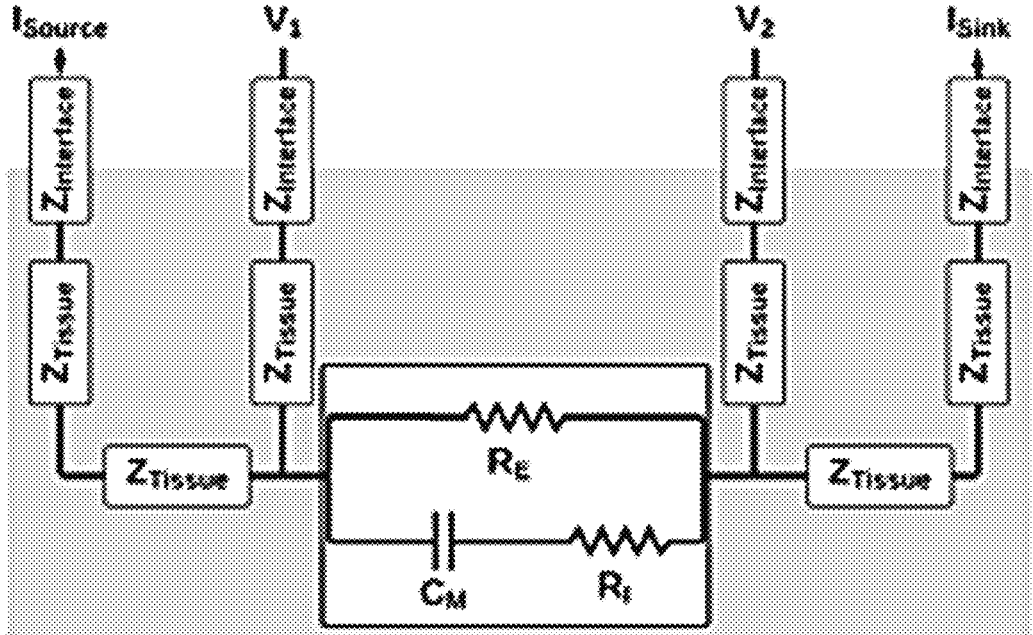

To validate the accuracy of our wearable BIS system electronics, the impedances of three tissue model circuits (Model 1: $R_E=R_I=191\Omega$, $C_m=10$ nF; Model 2: $R_E=R_I=309\Omega$, $C_m=8.2$ nF; and Model 3: $R_E=R_I=412\Omega$, $C_m=6.8$ nF) were measured with the device, and the results compared to the expected circuit model impedance. FIG. 3B illustrates an example of the tissue circuit equivalent model for four electrode bioimpedance sensing. 680Ω resistors were used to represent both $Z_{Tissue}$ and $Z_{Interface}$ in the four-electrode measurement model. For example, the system can be configured to collect data with the device sweeping from 5 kHz to 195 kHz in 39 steps at an ODR of 24 Hz and an FFT length of 8192, and the root mean square error (RMSE) was calculated.

Figures 3C, 4:
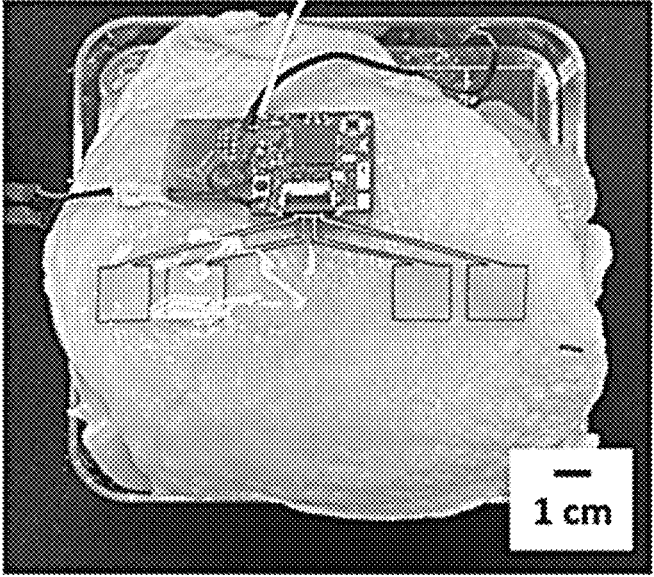
FIG. 3C illustrates examples of bioimpedance multivariate time series, in accordance with various embodiments of the present disclosure.
FIG. 4 is an image of the experimental setup for in-vitro validation, in accordance with various embodiments of the present disclosure.

The wearable system can perform bioimpedance spectroscopy (active sensing) that directly measures the body's two water compartments: extracellular and intracellular, thereby providing cellular level hydration assessment. The wearable system can produce continuous measurements that generate a bioimpedance profile unique to each individual that captures the impedance fluctuations from the extracellular water and intracellular water compartments. FIG. 3C shows an example of the continuous, multivariant time series measurements (bioimpedance profile data) from the wearable sensor outputs across difference frequencies.

In-Vitro Tissue Validation. To demonstrate the feasibility of detecting water loss in a biological tissue model, three excised fresh chicken thighs (260.3 g, 250.5 g, 215.0 g) with skin and bone intact were used to test the wearable bioimpedance sensing system. Each sample was kept at room temperature with a sensor attached for 80 min. FIG. 4 is an image of the experimental setup for in-vitro validation on excised chicken tissue. After every 20 min, excess water exudation on the tissue surface was wiped off with tissue paper, the sample was weighed, and a measurement of bioimpedance was taken. Parametric curve fitting was used to find the equivalent tissue circuit model $R_E$, $R_I$, and $C_m$ at each time point. The characteristic frequency can be calculated as follows:

$$f_c = \frac{1}{2\pi \cdot C_m(R_I + R_E)}$$

Results

Wearable System Electronics. At a typical operating point of the device, a 39-point sweep at an ODR of 24 Hz and an FFT length of 8192 gives a sweep period of 1.625 s. At this operating point, while measuring and transmitting data over BLE, the wearable system consumed 30.4 mW of power and is estimated to run for 18 hours with the 150 mAh LiPo battery. While the BIS front end was inactive, the system consumed 15.6 mW; so duty cycling the data acquisition can further increase the battery life. For example, sampling for 10 s every minute can extend the battery life to about 30.7 hours. The overall size of the electronic system is 20 mm×26 mm×7.4 mm and weighs 12.1 g.

Figure 5A:
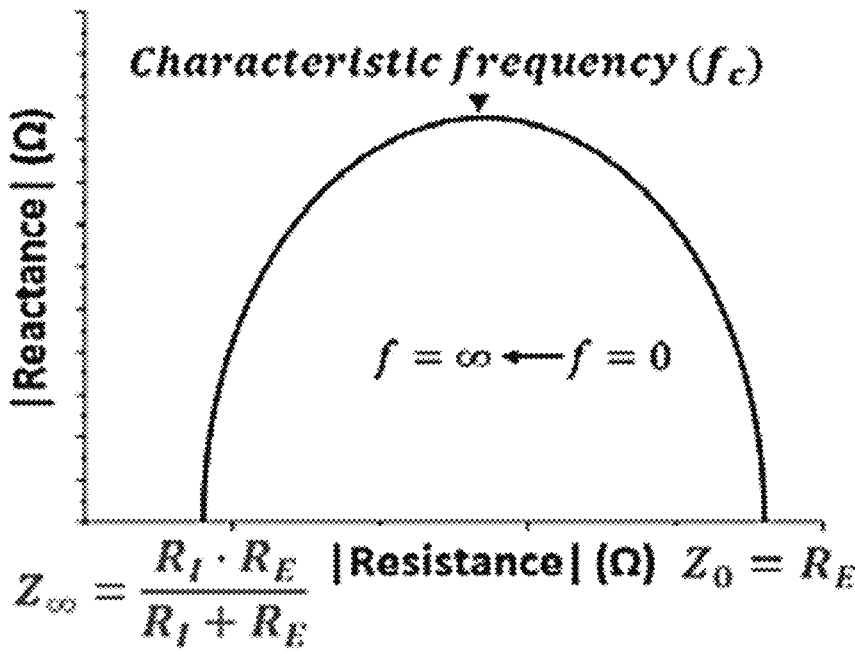
FIGS. 5A and 5B illustrate examples of Cole-Cole plot of impedance for the tissue circuit equivalent model and comparison with measured impedances, in accordance with various embodiments of the present disclosure.
Figure 5B:
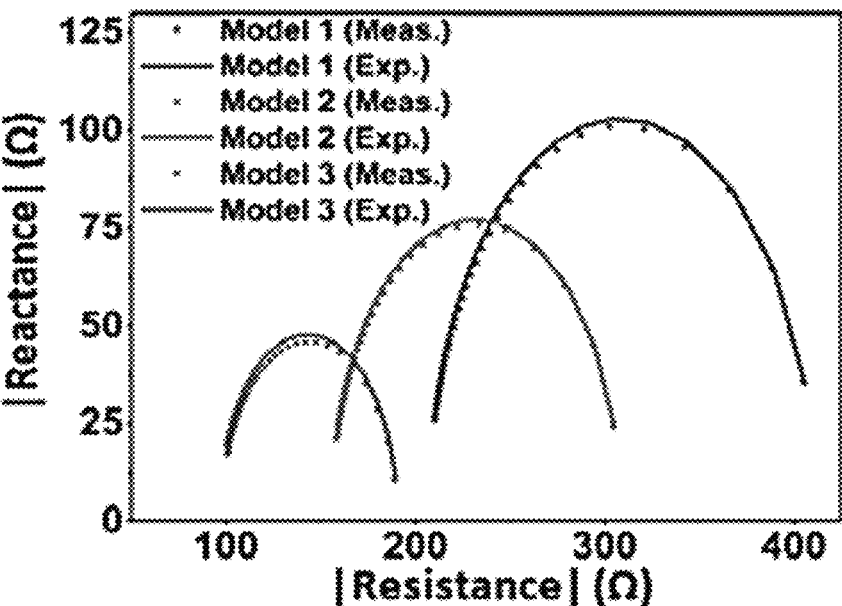

Circuit Model Validation. For the tissue equivalent circuit models measured with our device, the Cole-Cole plots are shown in FIGS. 5A and 5B. FIG. 5A illustrates an example of the Cole-Cole plot of impedance for the tissue circuit equivalent model and FIG. 5B compares examples of expected and measured impedances for the circuit models. The mean resistance RMSE across all models was 0.971Ω, and mean reactance RMSE across all models was 2.173Ω. Reactance RMSE increased with increasing frequency, with minimum mean reactance RMSE of 0.482Ω at 5 kHz and maximum mean reactance RMSE of 3.178Ω at 195 kHz.

Figure 6A:
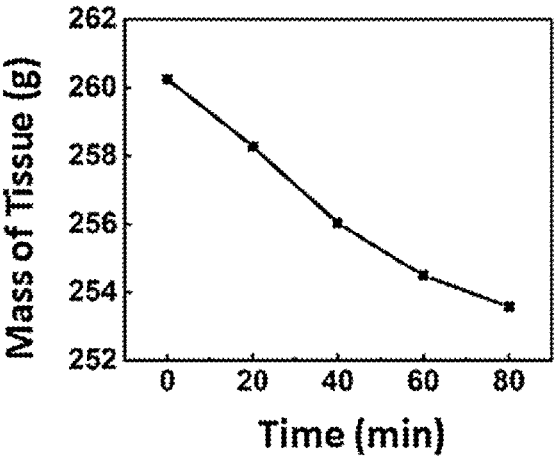
FIGS. 6A and 6B illustrate examples of weight change and tissue impedance of the excised chicken tissue of FIG. 4 over time, in accordance with various embodiments of the present disclosure.
Figure 6B:
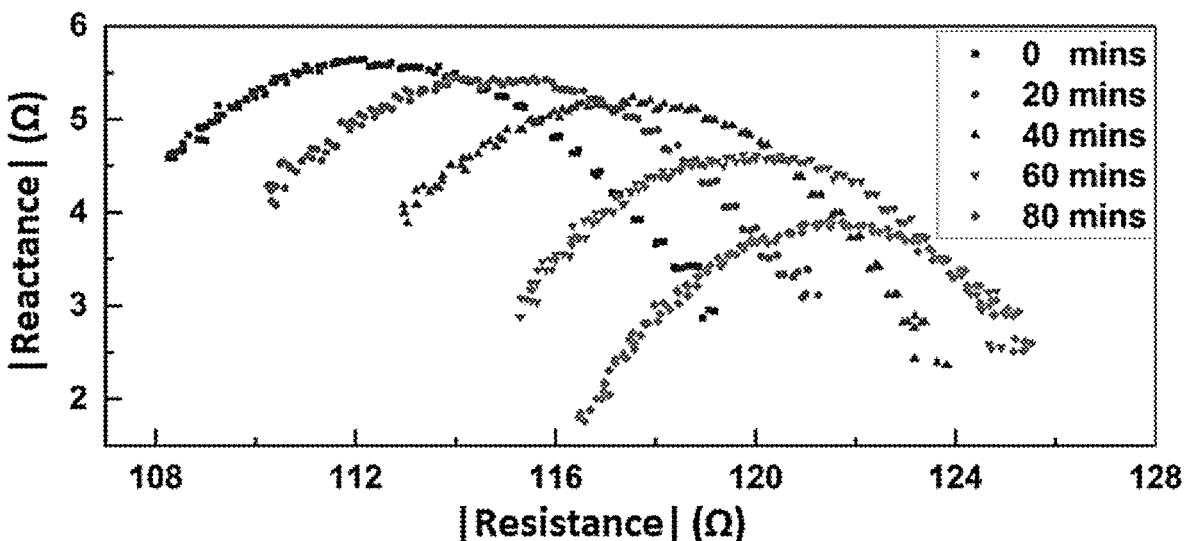
Figure 7A:
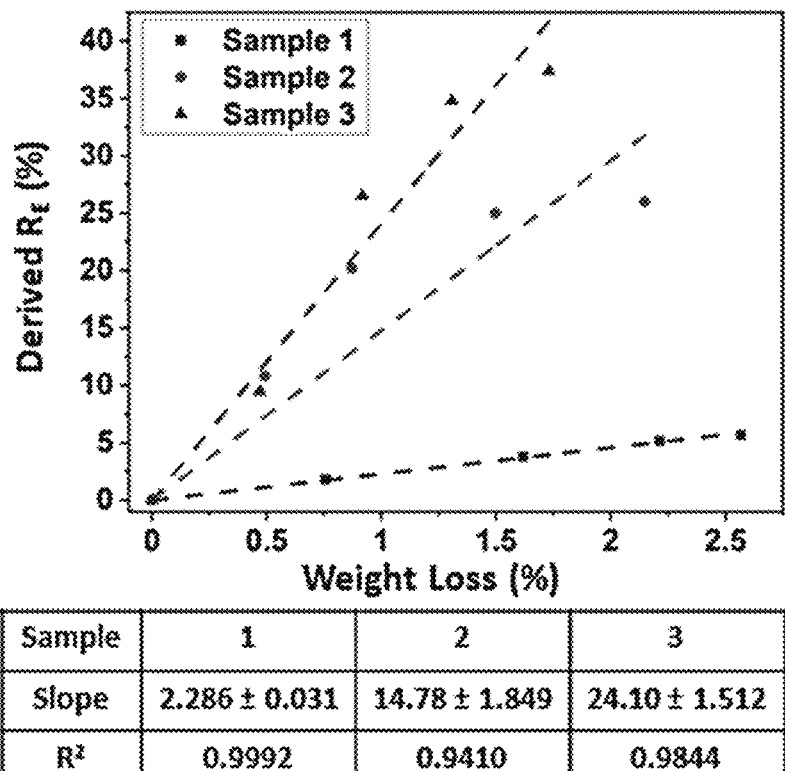
FIGS. 7A-7D illustrate examples of percent change in derived model parameters versus relative tissue weight loss, in accordance with various embodiments of the present disclosure.
Figure 7B:
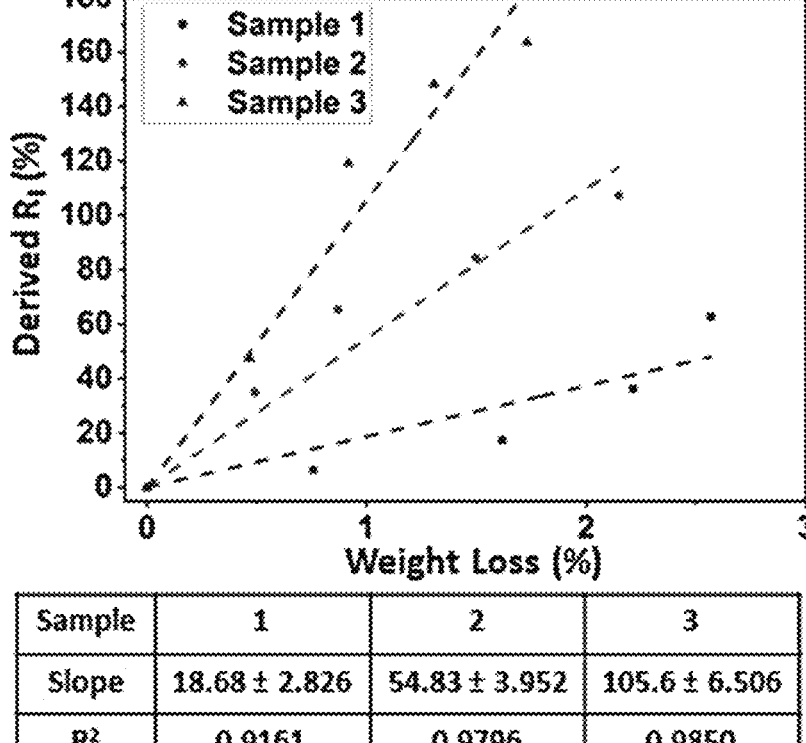
Figure 7C:
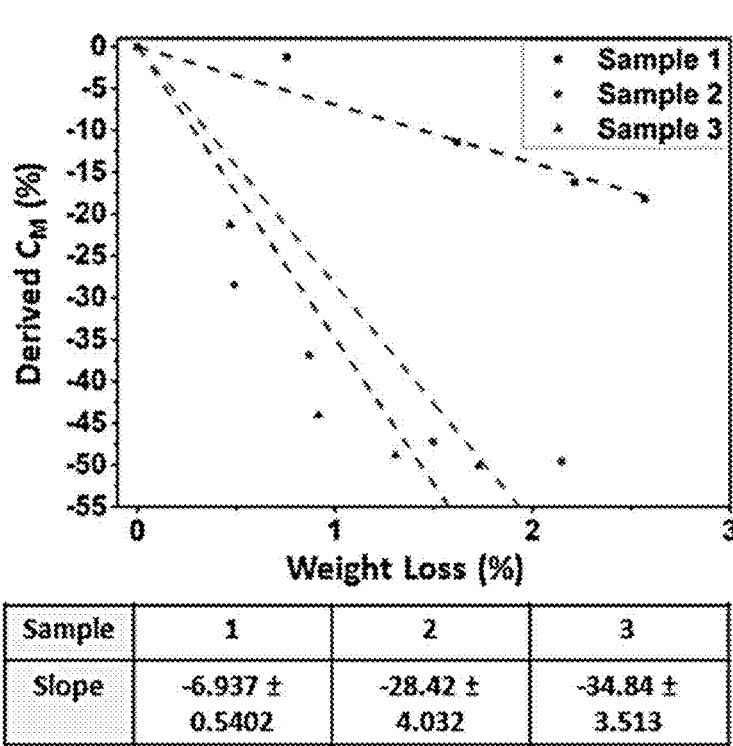
Figure 7D:
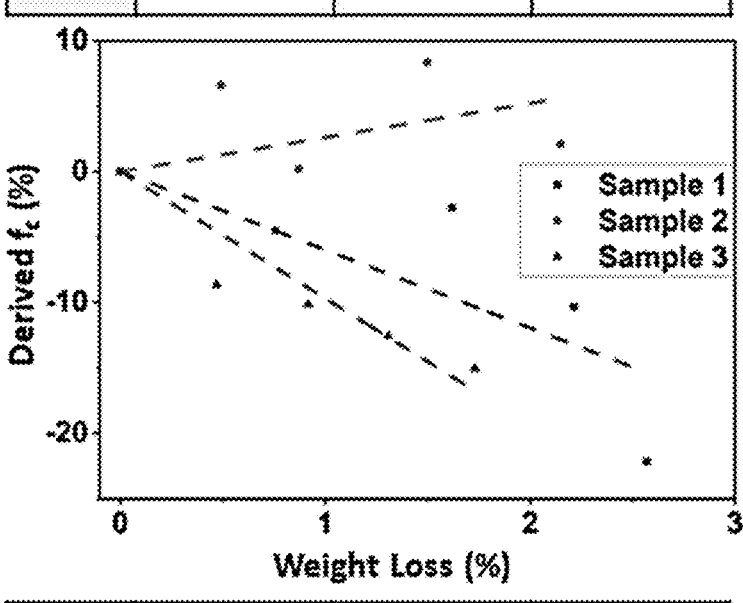

In-Vitro Tissue Validation. FIG. 6A illustrates the weight change of the excised chicken tissue of FIG. 4 over time. The decrease of weight is shown with respect to time due to moisture loss for one of the samples and the change in impedance over time. FIG. 6B illustrates a Cole-Cole plot of the tissue impedance over time. The tissue model circuit parameters derived from parametric fitting were compared with the percentage weight loss over time for each sample. Different baseline levels of parameter fit were observed due to differences in weight and composition of each sample, so the weights and circuit parameters were normalized by their value at time t=0. For each sample, an increase in extracellular fluid resistance $R_E$ and intracellular fluid resistance $R_I$, and a decrease in membrane capacitance $C_m$ were observed with weight loss. FIGS. 7A-7D illustrate percent change in derived model parameters versus relative tissue weight loss. FIG. 7A illustrates an example of extracellular resistance $R_E$, FIG. 7B illustrates an example of intracellular resistance $R_I$, FIG. 7C illustrates an example of cellular membrane capacitance $C_m$, and FIG. 7D illustrates an example of characteristic frequency $f_c$. A strong negative linear relationship between characteristic frequency and weight loss was observed except for one of the samples in FIG. 7D.

Figures 8A, 8B:
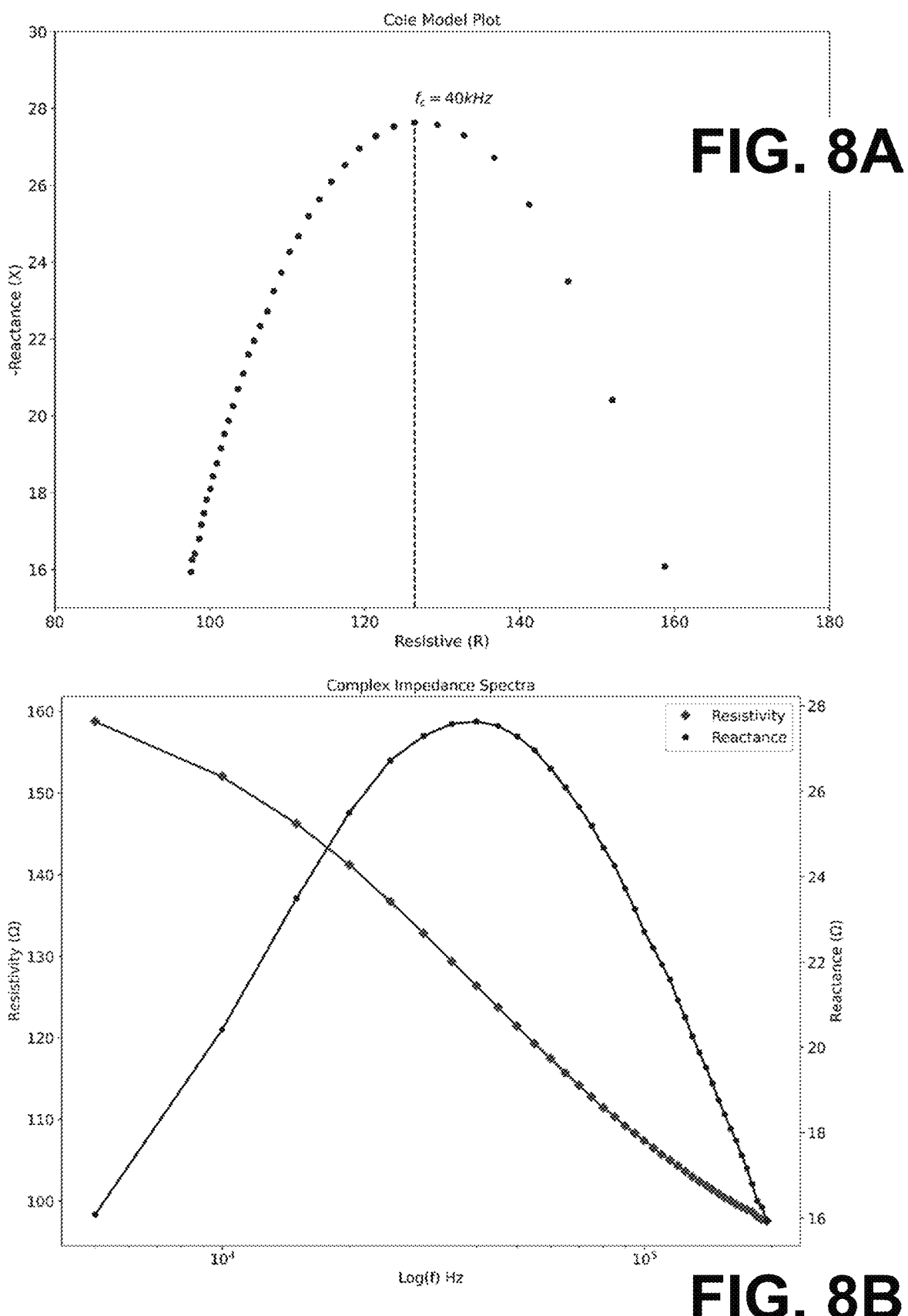
FIGS. 8A-8D illustrate examples of bioimpedance measurements from a human subject, in accordance with various embodiments of the present disclosure.
Figures 8C, 8D:
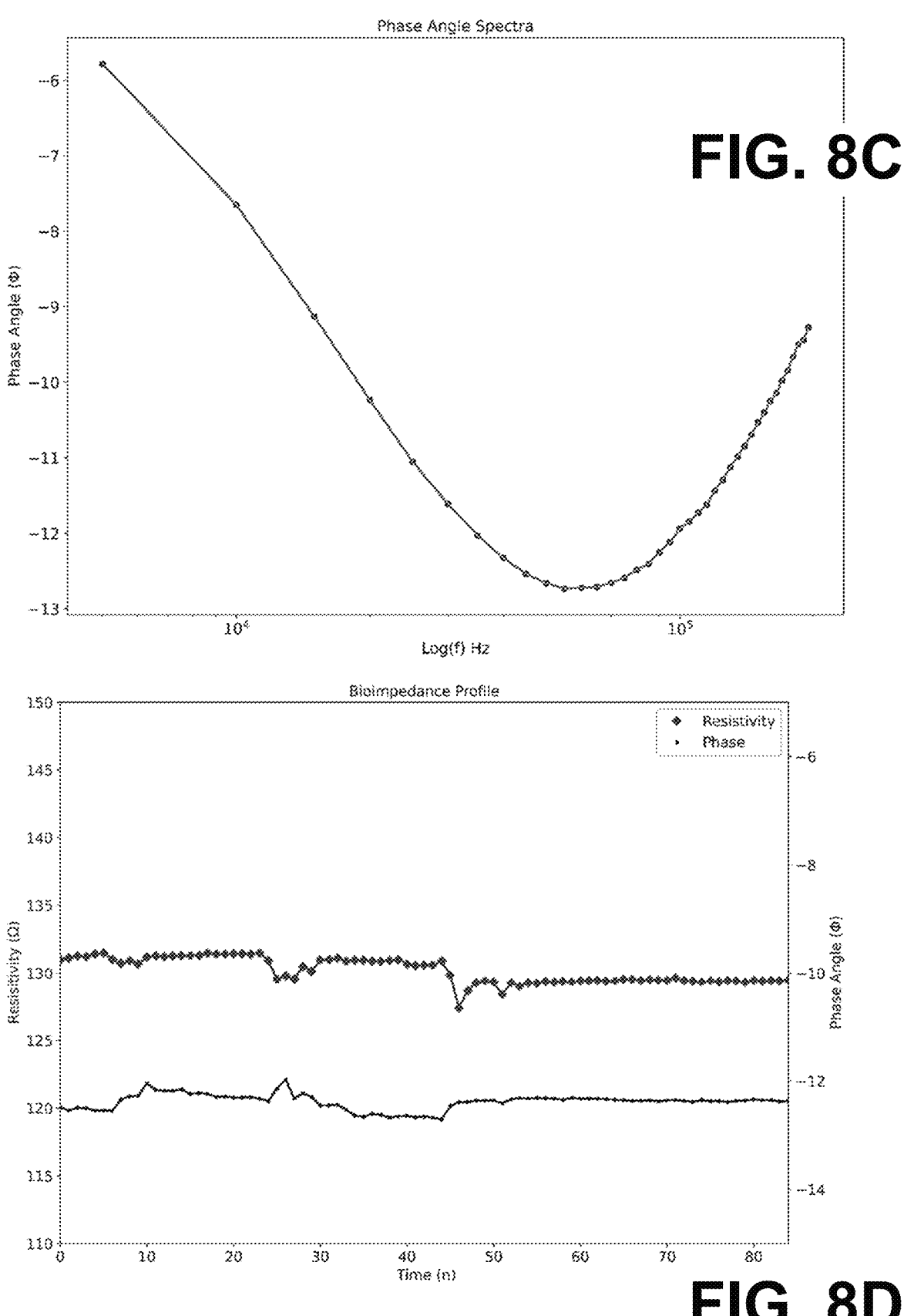

FIGS. 8A-8D illustrate examples of bioimpedance measurements from a human subject. FIG. 8A illustrates the Cole-Cole plot with the estimated characteristic frequency. FIG. 8B illustrates the complex impedance spectra versus log frequency. FIG. 8C illustrates the phase angle versus log frequency. FIG. 8D illustrates a representative example of continuous measurements comprising a bioimpedance profile.

A wireless wearable bioimpedance spectroscopy system comprising a custom miniaturized electronic system and a conformable AgNW electrode sensor capable of continuous monitoring of tissue hydration has been presented. Proof-of-concept in-vitro experiments were performed to demonstrate the successful operation of the overall system. In-vivo validation against a gold standard hydration sensing device can be carried out on subjects with various hydration levels and body compositions. Advanced signal processing and machine learning techniques can be included to isolate hydration level in bioimpedance spectroscopy measurements from other potentially confounding factors such as motion artifacts, activity levels and physiological signals.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

The term "substantially" is meant to permit deviations from the descriptive term that don't negatively impact the intended purpose. Descriptive terms are implicitly understood to be modified by the word substantially, even if the term is not explicitly modified by the word substantially.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

The invention claimed is:

1. A wearable monitoring system, comprising:
   a plurality of electrodes comprising one or more current source electrode, one or more current sink electrode, and at least two voltage measurement electrodes aligned between the current source and sink electrodes, the plurality of electrodes being conformal and stretchable nanowire (NW) electrodes; and
   processing circuitry configured for bioimpedance sensing based upon excitation current applied through the current source and sink electrodes and measured voltage obtained through the at least two voltage measurement electrodes across a range of excitation frequencies, the processing circuitry comprising excitation voltage circuitry coupled to the one or more current source electrode, voltage measurement circuitry coupled to the at least two voltage measurement electrodes, and current measurement circuitry coupled to the one or more current sink electrode, the processing circuitry comprising an impedance analog front end (AFE) coupled to the plurality of electrodes thereby providing direct current (DC) isolation for each of the one or more current source electrode, the one or more current sink electrode, and the at least two voltage measurement electrodes.

2. The system of claim 1, wherein the measurements are obtained at a plurality of frequencies in the range of excitation frequencies.

3. The system of claim 2, wherein the processing circuitry calculates an impedance at each of the plurality of frequencies.

4. The system of claim 1, wherein the nanowire electrodes comprise a network of silver nanowires (AgNWs).

5. The system of claim 4, wherein the AgNWs are inlaid in a soft polymer matrix.

6. The system of claim 5, wherein the soft polymer matrix comprises Poly(dimethylsiloxane) (PDMS).

7. The system of claim 1, wherein the one or more current source electrode, the one or more current sink electrode, and the at least two voltage measurement electrodes each have a defined area and a defined spacing between the other electrodes.

8. The system of claim 1, wherein the processing circuitry calculates an impedance at each of a plurality of frequencies within the range of excitation frequencies.

9. The system of claim 8, wherein the processing circuitry transmits data associated with the impedance to a remotely located data aggregator.

10. The system of claim 1, wherein the processing circuitry comprises an accelerometer and the transmitted data comprises motion data obtained from the accelerometer.

11. A method for bioimpedance sensing, comprising:
    positioning a wearable monitoring system on a surface, the wearable monitoring system comprising a plurality of electrodes comprising one or more current source electrode, one or more current sink electrode, and at least two voltage measurement electrodes aligned between the current source and sink electrodes, the plurality of electrodes coupled to processing circuitry comprising excitation voltage circuitry coupled to the one or more current source electrode, voltage measurement circuitry coupled to the at least two voltage measurement electrodes, and current measurement circuitry coupled to the one or more current sink electrode, the processing circuitry comprising an impedance analog front end (AFE) coupled to the plurality of electrodes thereby providing direct current (DC) isolation for each of the one or more current source electrode, the one or more current sink electrode, and the at least two voltage measurement electrodes;

applying excitation current through the current source and sink electrodes over a range of excitation frequencies;

measuring voltage across the at least two voltage measurement electrodes over the range of excitation frequencies; and determining a bioimpedance based upon the applied excitation current and the measured voltage over the range of excitation frequencies.

12. The method of claim 11, wherein the measured voltage is obtained at a plurality of frequencies in the range of excitation frequencies.

13. The method of claim 12, wherein an impedance is calculated at each of the plurality of frequencies.

14. The method of claim 11, comprising transmitting data associated with the bioimpedance to a remotely located data aggregator.

15. The method of claim 14, comprising monitoring motion of the wearable monitoring system, wherein the transmitted data comprises motion data obtained by the wearable monitoring system.

16. The method of claim 11, wherein the surface is a skin surface.

17. The method of claim 11, wherein the plurality of electrodes comprises conformal and stretchable silver nanowire (AgNW) electrodes.

18. The method of claim 11, comprising producing multivariate time series measurements of the bioimpedance over the range of excitation frequencies.

19. The method of claim 18, comprising producing a bioimpedance profile with continuous resistivity and phase measurements over the range of excitation frequencies.

20. The method of claim 18, comprising directly measuring impedance of extracellular and intracellular water components over a small area of the surface.

\* \* \* \* \*